(12) United States Patent
Richard et al.

(10) Patent No.: US 6,432,357 B1
(45) Date of Patent: Aug. 13, 2002

(54) STERILIZING GAS COMPOSITIONS OF ETHYLENE OXIDE, PENTAFLUOROETHANE AND HEPTAFLUOROPROPANE

(75) Inventors: Robert G. Richard; Barbara Ruth Decaire, both of Erie County, NY (US); Stephen Alan Conviser, Morristown, NJ (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 09/569,106

(22) Filed: May 11, 2000

Related U.S. Application Data

(63) Continuation of application No. 09/025,946, filed on Feb. 19, 1998, now abandoned.

(51) Int. Cl.⁷ .................................................. A61L 2/20
(52) U.S. Cl. ......................................... 422/34; 252/372
(58) Field of Search ..................... 422/34, 37; 252/372

(56) References Cited

U.S. PATENT DOCUMENTS

| 4,249,917 A | 2/1981 | Tarancon |
| 4,250,143 A | 2/1981 | Bryan et al. |
| 4,555,251 A | 11/1985 | Jonsson et al. |
| 4,822,563 A | 4/1989 | Joslyn |
| 4,954,284 A | 9/1990 | Batt et al. |
| 4,954,315 A | 9/1990 | Brahmbhatt |
| 4,971,716 A | 11/1990 | Batt et al. |
| 4,976,922 A | 12/1990 | Chippett et al. |
| 5,039,484 A | 8/1991 | Chippett et al. |
| 5,069,686 A | 12/1991 | Baker et al. |
| 5,149,500 A | 9/1992 | Brahmbhatt et al. |
| 5,254,309 A | 10/1993 | Felix et al. |
| 5,314,682 A | 5/1994 | Sweval et al. |
| 5,342,579 A | 8/1994 | Conviser ................... 422/34 X |
| 5,346,669 A | 9/1994 | Sweval ......................... 422/34 |
| 5,376,333 A | 12/1994 | Shankland et al. |
| 5,510,377 A | 4/1996 | Deger ....................... 422/34 X |
| 5,674,451 A | 10/1997 | Nimitz ......................... 422/34 |
| 5,698,011 A | 12/1997 | Chung et al. |
| 5,874,113 A | 2/1999 | Conviser et al. |
| 5,900,185 A | 5/1999 | Tapscott |
| 5,976,554 A | 11/1999 | Richard et al. |
| 6,132,679 A | 10/2000 | Conviser |

FOREIGN PATENT DOCUMENTS

| DE | 1811307 | 7/1969 |
| DE | 1931116 | 12/1970 |
| DE | 19708669 A1 | 9/1998 |
| EP | 130319 | 1/1985 |
| EP | 1040840 A1 | 10/2000 |
| FR | 1288568 | 5/1969 |
| FR | 2404438 | 6/1979 |
| HU | 9601405 | 12/1997 |
| WO | WO 93/23086 | 11/1993 |
| WO | WO 95/32007 | 11/1995 |
| WO | WO 96/13281 | 5/1996 |
| WO | WO 97/14446 | 4/1997 |
| WO | WO 99/42143 | 8/1999 |
| WO | WO 99/42144 | 8/1999 |
| WO | WO 00/27441 | 5/2000 |

*Primary Examiner*—Elizabeth McKane
(74) *Attorney, Agent, or Firm*—Deborah Chess

(57) ABSTRACT

Non-flammable sterilizing gas compositions of ethylene oxide and a flame suppressant comprising pentafluoroethane and heptafluoropropane are useful in the gaseous sterilization of heat and/or moisture sensitive materials. The sterilizing gas compositions are environmentally acceptable and are more efficient and safer to use than conventional sterilant gas mixtures.

15 Claims, No Drawings

STERILIZING GAS COMPOSITIONS OF ETHYLENE OXIDE, PENTAFLUOROETHANE AND HEPTAFLUOROPROPANE

This application is a continuation of Ser. No. 09/025,946 filed Feb. 19, 1998 now abandoned.

FIELD OF THE INVENTION

The invention relates generally to the field of sterilization and more particularly to sterilizing gas compositions comprising ethylene oxide, pentafluoroethane and heptafluoropropane.

BACKGROUND OF THE INVENTION

Sterilization by the application of boiling water or steam to the article to be sterilized has been carried out for many years. More recently the need to employ a different sterilant has arisen because certain articles, particularly those employed in the medical and aerospace industries, cannot withstand the temperatures or the moisture associated with steam sterilization.

Ethylene oxide (EO) has become widely used as a sterilant because it is highly effective and its residues are less likely to be absorbed by or adsorbed to the articles being sterilized because they volatilize quickly. By itself, ethylene oxide is an extremely flammable gas. It has a flash point less than −20° F., and forms explosive mixtures in air from about 3.0 volume percent to 100 volume percent ethylene oxide. Thus, when ethylene oxide is used alone as a sterilizing gas, precautions such as explosion proof equipment are mandatory.

A preferable practice is to blend the ethylene oxide with an inert carrier gas or flame suppressant composition which serves to dilute the ethylene oxide and render the mixture as a whole, nonflammable. If the inert component is truly inert, i.e. it does not participate chemically in the combustion process, then the extinguishing efficiency of the inert species depends on such physical properties as its specific heat and thermal conductivity, see for example H. F. Coward and G. W. Jones "Limits of Flammability of Gases and Vapors", Bulletin 503 p. 5 (1952). The physical extinction mechanism relies upon removal of the energy required to maintain combustion.

The flammability properties of ethylene oxide/halocarbon blends do not follow this simple physical correlation-rather, it is well known their extinctive properties stem from a chemical mechanism whereby the halogen species chemically participates in the combustion reaction, and interferes with or inhibits the combustion reaction. R. Hirst states in *Institution Of Fire Engineers Quarterly*, vol. 25 (No. 59) Sep. 1965 p. 231–250, that the extinguishing ability of halogen species follows the order I>Br>Cl>F. Iodine containing halocarbons are generally known to be less chemically stable and more toxic than other members of the halocarbon family. The bromine containing species are known to possess a much greater ozone depletion potential than their chlorine containing analogs. For environmental reasons, potential halocarbon carrier gases are restricted to the hydrohalocarbons containing fluorine and/or chlorine. A hydro-substituted halocarbon possesses a much lower atmospheric lifetime than a fully halogenated chlorofluorocarbon. However, decreasing the halogen content of the carrier gas, by incorporating hydrogen in the molecule, would tend to reduce the flammability suppressant or extinctive properties of the carrier gas.

Over the last two decades the flame suppressant of choice for use with ethylene oxide in a sterilant mixture has been dichlorodifluoromethane (known in the industry as CFC-12). Recently, however, CFC-12 has come under scrutiny because it is one of the chlorofluorocarbons believed to cause significant damage to the ozone layer in the upper atmosphere. Accordingly, worldwide reduction and elimination of the use of CFC-12 is now underway.

Carbon dioxide is another flame suppressant known for use with ethylene oxide in a sterilant mixture. Because of the characteristics of carbon dioxide, however, a non-flammable ethylene oxide/carbon dioxide mixture contains less than 40 percent of the ethylene oxide per unit volume as an ethylene oxide/CFC-12 mixture. Thus, sterilization must be carried out either at higher pressures or for longer contact time. Furthermore, the large difference in the vapor pressures of ethylene oxide and carbon dioxide causes the mixture to separate upon withdrawal from the storage tank or cylinder, raising the danger of delivering a sterilant mixture rich in carbon dioxide, which will not sterilize, or rich in ethylene oxide, which is explosive.

A short term solution to the concern over the ozone depletion effects of CFC-12 has been to employ hydrochlorofluorocarbons (HCFCs), which have a reduced chlorine content. Known ethylene oxide sterilant gas mixtures include 1-chloro-1, 2, 2, 2-tetrafluoroethane (HCFC-124), chlorodifluoromethane (HCFC-22) and mixtures thereof. OXYFUME® 2002, commercially available from Allied-Signal Inc., is a widely used sterilant mixture comprising HCFC-124 and HCFC-22. Due to the presence of chlorine, however, such compositions still have a potential for stratospheric ozone depletion.

Hydrofluorocarbons (BFCs) do not contain chlorine and have ozone depletion potentials ("ODPs") of nearly zero. They are considered to be environmentally acceptable. However, not all hydrofluorocarbons are suitable as flame suppressants in ethylene oxide gas mixtures. Simple substitution of an arbitrary nonflammable gas does not necessary ensure a useful sterilizing gas mixture. For example, 1, 1, 1, 2-tetrafluoroethane (HFC-134a), generally accepted as the most likely replacement for CFC-12, is not an effective flame suppressant in ethylene oxide gas mixtures. It has been suggested that the additional hydrogen atoms may contribute to its flammability.

As a first consideration, the flammability properties of the gas mixture must be such that sufficient ethylene oxide is delivered by the mixture to effect the sterilization in an appropriate time. The Association for the Advancement of Medical Instrumentation (AAMI) recommends an absolute minimum ethylene oxide concentration of 400 mg/liter. If the carrier gas does not mask the flammability to a sufficient extent, a lower concentration of ethylene oxide must be used to ensure non-flammability. In such cases, either a longer exposure time is required to perform the sterilization, which affects productivity, or greater operating pressures are required to increase the effective ethylene oxide density in the sterilization chamber. Increasing the operating pressure is generally not a viable option because existing sterilization chambers may not be rated for the increased pressure. Furthermore, increased pressure can lead to swelling and rupture of the sealed plastic bags commonly used to package disposable medical devices. Ideally, the sterilization is performed using the highest safe concentration of ethylene oxide in order to minimize cycle time.

As an additional consideration, a candidate flame suppressant must also be miscible with ethylene oxide in the liquid phase and must not segregate from the ethylene oxide to any great extent during vaporization. Segregation or fractionation can lead to potentially flammable or explosive situations. The degree of segregation that may occur during evaporation is related to the relative volatility of the components of the mixture. The vapor pressure of ethylene oxide at 70° F. is 22 psia. A very large difference in volatility between ethylene oxide and the candidate flame suppressant increases susceptibility for the sterilant gas mixtures to fractionate.

As yet another consideration, the vapor pressure of a candidate hydrofluorocarbon may be too high and the resultant ethylene oxide gas mixture may not be suitable for use with conventional low pressure cylinders.

As can be appreciated from the above, there remains a continuing need in the art for sterilizing gas mixtures that are non-flammable yet contain sufficient ethylene oxide for effective, rapid sterilization; are miscible; are environmentally acceptable; provide sufficient vapor pressure to deliver the liquid mixture to the sterilization chamber but not too high a vapor pressure for standard shipping cylinders; are safer to use; and are cost effective.

DETAILED DESCRIPTION OF THE INVENTION AND PREFERRED EMBODIMENTS

The invention provides sterilizing gas and methods for using the compositions.

In one embodiment, the invention provides sterilizing gas compositions comprising ethylene oxide and a flammability suppressant which comprises, consists essentially, or consists of pentafluoroethane and heptafluoropropane.

In a preferred embodiment, the invention provides sterilizing gas compositions comprising ethylene oxide and a flammability suppressant which comprises pentafluoroethane and 1, 1, 1, 2, 3, 3, 3-heptafluoropropane.

In yet another preferred embodiment, the invention provides sterilizing gas compositions comprising from about 1.7 to about 11, preferably about 6 to about 11, weight percent ethylene oxide and from about 98.3 to about 89, preferably about 95 to about 89, weight percent of a flammability suppressant which comprises, consists essentially of; or consists of pentafluoroethane and heptafluoropropane, wherein the pentafluoroethane is present in an amount of about 1 to about 99, preferably about 15 to about 95, still preferably about 85 to about 95, weight percent and wherein the heptafluoropropane is present in an amount of about 99 to about 1, preferably about 85 to about 5, still preferably about 15 to about 5, weight percent, based on the total amount of pentafluoroethane and heptafluoropropane present.

In yet another preferred embodiment of the invention, sterilizing gas compositions are provided comprising about 10.4 weight percent ethylene oxide and about 89. 6 weight percent of a flammability suppressant which comprises, consists essentially of, or consists of pentafluoroethane and heptafluoropropane, wherein the pentafluoroethane is present in an amount of about 91.4 weight percent and the heptafluoropropane is present in an amount of about 8.6 weight percent, based on the total amount of pentafluoroethane and heptafluoropropane present.

In another embodiment of the invention, a method for sterilizing articles is provided, which method comprises exposing the articles to a sterilizing gas composition comprising ethylene oxide and a flammability suppressant which comprises, consists essentially of, or consists of pentafluoroethane and heptafluoropropane.

In accordance with the invention, novel sterilizing gas compositions comprising ethylene oxide, pentafluoroethane and heptafluoropropane having improved flammability suppressant characteristics have been discovered. The novel sterilizing gas compositions contain an inert blend of fluorocarbon diluents, which is miscible with ethylene oxide, compatible with plastics and polymers used in the construction of medical devices and is considered to be environmentally acceptable. The sterilizing gas compositions of the present invention have sufficient vapor pressure to deliver the liquid mixture to the sterilization chamber and can be shipped in standard cylinders. The sterilizing gas compositions of the present invention advantageously provide a gas phase concentration of ethylene oxide equivalent to or in excess of that concentration provided by commercially available OXYFUME® 2002 sterilant mixture, with improved safety margins. An additional advantage of the greater gas phase concentration is that fewer pounds of sterilizing gas composition are required per cycle. A particularly surprising advantage of the sterilizing gas compositions of the present invention is that sterilization occurs faster than with commercially available sterilant mixtures that have the same ethylene oxide (active ingredient) concentrations.

Other features and advantages of the present invention will become apparent from the following description of the invention.

The components of the composition of the invention are known materials that are commercially available or may be prepared by known methods. Preferably, the components are of sufficiently high purity so as to avoid the introduction of adverse influence on the properties of the system.

Heptafluoropropane occurs as two separate isomers, 1, 1, 1, 2, 3, 3, 3-heptafluoropropane (HFC-227ea) and 1, 1, 1, 2, 2, 3, 3 -heptafluoropropane (HFC-227ca). Either isomer or a mixture of the two is suitable for the purposes of the invention. HFC-227ea is preferred.

Other components may be present in the sterilant mixture, including inert propellants which may be employed to increase the pressure in the sterilant cylinder and facilitate propelling of the mixture into the sterilization chamber. Suitable propellants include nitrogen, carbon dioxide, argon and trifluoromethane.

The sterilant mixtures of the present invention may be prepared using any effective mixing technique known to those skilled in the art. Generally, the three components are physically combined as a liquefied gas composition in cylinders. When in use the liquid phase is expelled into a heat exchanger where it is vaporized and then introduced into the sterilizing chamber. The selection of an appropriate process for the production of a particular sterilant mixture may be accomplished by one skilled in the art without undue experimentation.

The sterilant mixtures of the present invention may be used to sterilize a wide variety of articles, including medical equipment such as syringes, needles, gloves, ampules, dressings, suture, scalpels, catheters, metal or glass containers, etc. The sterilant mixtures may also be used to sterilize rubber and plastic goods, and can be employed as fumigants for materials including furs, bedding, paper goods and other equipment. The sterilant mixtures of the present invention are effective against insects, bacteria, fungi and various other microorganisms.

In the process embodiment of the invention, the sterilizing gas compositions of the present invention may be used in any manner well known in the art by essentially exposing the articles to be sterilized to the sterilizing gas under conditions and for a period of time necessary to achieve a desired degree of sterility. Typically, the gaseous sterilization process is effected by placing the articles to be sterilized in a chamber, evacuating the chamber, humidifying the chamber, admitting the sterilizing gas composition at an appropriate pressure and temperature, maintaining contact between the sterilizing atmosphere and the articles to be sterilized for an appropriate period of time, and finally discharging and evacuating the chamber to remove the sterilant gas. Although there are many variations on the basic process, the major factors which have to be controlled in order to effect the sterilization are exposure time, temperature, ethylene oxide pressure or partial pressure and relative humidity, all of which may be selected by those skilled in the art without undue experimentation.

Sterilizing gas compositions of the present invention may be used with any commonly employed sterilizer known to the art such as those described in detail in U.S. Pat. No. 5,039,484 to Chippett et al. and U.S. Pat. No. 5,039,485 to Conviser et al.

The following examples serve to further illustrate or distinguish the invention and are not intended to be limiting.

EXAMPLES

Example 1

Efficacy testing was performed to compare an ethylene oxide/(HFC-125/HFC-227ea) sterilizing gas composition of the present invention to commercially available OXYFUME® 2002. AAMI (Association for the Advancement of Medical Instrumentation) test challenge packs were prepared by placing one chemical indicator and two syringes containing biological indicators in an 18"×30" towel that has been folded lengthwise and then in half; the "pack" was then folded into a first 24"×24" wrap; and then a second 24"×24" wrap. Sterilization (using 300, 450, 600 and 750 mg/l) of thus prepared test challenge packs was performed under standard conditions of 130° F. and 40–60% RH. All sterilizer loads were conditioned using the same 24–26" HG vacuum, 120–135° F., 40–60% humidity and 30–35 minutes. The half cycle time was determined by decreasing the exposure time until at least one out of a million microorganisms on the biological indicator survived. This time is called the half cycle time because it is doubled to obtain the cycle time needed to ensure sterilization.

| AAMI Pack Half Cycle Time (minutes) | | | | |
|---|---|---|---|---|
| Composition | 300 mg/l | 450 mg/l | 600 mg/l | 750 mg/l |
| OXYFUME ® 2002 EO/HCFC-124/HCFC-22 (10/63/27 wt. %) | 90 | 90 | ≦60 | 45 |
| EO/HFC-125/HFC-227ea (10.4/91.9/7.7 wt. %) | 45 | 35 | 30 | 15 |

The above table shows that the sterilizing gas compositions of the present invention surprisingly sterilize in 30 to 50% of the time required for the conventional sterilant mixture at the same ethylene oxide (active ingredient) concentration.

Example 2

The sterilizing gas compositions of the present invention were tested for flammability using ASTM E681-94, modified to use a 12 liter flask and a spark ignition.

| Composition | Maximum wt. % EO without becoming flammable |
|---|---|
| EO/(HFC-125/HFC-227ea 91.5/8.5 wt. %) | 10.6 |
| EO/(HFC-125/HFC-227ea 91.5/8.5 wt. %) | 10.2 |

Example 3

Vapor pressures are measured using a calibrated Bourden gauge accurate to ±1%. Mixtures prepared gravimetrically and allowed to reach thermal equilibrium in a temperature controlled water bath before determining the vapor pressure. Nonflammable HFC-125/HFC-227/ethylene oxide blends possess vapor pressures greater than 10 psig, which is sufficient to expel the material from the cylinder at 21.1° C. into a 10 psig sterilizing chamber.

Example 4

A glass tube is sealed containing a mixture of ethylene oxide in pentafluoroethane-heptafluoropropane. One liquid phase is observed to exist from room temperature down to −10° C. This example shows that BFC-125/HFC-227 is miscible with ethylene oxide. Therefore, when the liquid phase is removed its composition is consistent and nearly constant.

Example 5

Compatibility tests are performed by exposing the test material to the fluorocarbon vapor at 24.7 psia and 130° F. for 16 hours. At the end of the exposure period any change in weight of the part is determined and a visual inspection is performed. Parts are examined for any signs of deterioration such as crazing, cracking, discoloration or clouding. Study materials include: Polypropylene/LEXAN, Polycarbonate/LEXAN, Polystyrene, Polypropylene, Latex/Silicone Rubber, PVC, Cotton Gauze and Synthetic Skin. The data indicate plastics and polymers commonly used in the construction of medical devices, which are incompatible with certain fluorocarbons, show no deleterious effect when exposed to HFC-125/HFC-227.

What is claimed is:

1. Sterilizing gas compositions comprising ethylene oxide and a flammability suppressant which comprises pentafluoroethane and heptafluoropropane.

2. The sterilizing gas compositions of claim 1 comprising from about 1.7 to about 11 weight percent ethylene oxide and from about 98 to about 89 weight percent of a flammability suppressant which comprises pentafluoroethane and heptafluoropropane.

3. The sterilizing gas compositions of claim 2 wherein the ethylene oxide is present in an amount of about 6 to about 11 weight percent.

4. The sterilizing gas compositions of claim 3 wherein the pentafluoroethane is present in an amount of about 99 to about 1 weight percent and the heptafluoropropane is present in an amount of about 1 to about 99 weight percent, based on the total amount of pentafluoroethane and heptafluoropropane present.

5. The sterilizing gas compositions of claim 4 wherein the pentafluoroethane is present in an amount of about 95 to about 15 weight percent and the heptafluoropropane is present in an amount of about 5 to about 85 weight percent, based on the total amount of pentafluoroethane and heptafluoropropane present.

6. The sterilizing gas compositions of claim 5 wherein the pentafluoroethane is present in an amount of about 95 to about 85 weight percent and the heptafluoropropane is present in an amount of about 5 to about 15 weight percent, based on the total amount of pentafluoroethane and heptafluoropropane present.

7. The sterilizing gas compositions of claim 6 wherein the pentafluoroethane is present in an amount of about 91.4 weight percent and the heptafluoropropane is present in an amount of about 8.6 weight percent.

8. The sterilizing gas compositions of claim 7 wherein the heptafluoropropane is 1, 1, 1, 2, 3, 3, 3 -heptafluoropropane.

9. The sterilizing gas compositions of claim 1 further comprising an inert propellant.

10. The sterilizing gas compositions of claim 9 wherein the inert propellant is selected from the group consisting of nitrogen, carbon dioxide, argon and trifluoromethane.

11. The sterilizing gas compositions of claim 10 wherein the inert propellant is nitrogen.

12. The sterilizing gas compositions of claim 1 wherein the flammability suppressant consists essentially of pentafluoroethane and heptafluoropropane.

13. The sterilizing gas compositions of claim 12 wherein the heptafluoropropane is 1, 1, 1, 2, 3, 3, 3- heptafluoropropane.

14. A method for sterilizing articles comprising the step of exposing the articles to a sterilizing gas composition comprising ethylene oxide and a flammability suppressant which comprises pentafluoroethane and heptafluoropropane.

15. A method for sterilizing articles comprising the step of exposing the articles to the sterilizing gas compositions of claim 8.

* * * * *